United States Patent [19]
Milo

[11] Patent Number: 5,607,470
[45] Date of Patent: Mar. 4, 1997

[54] SUTURE RINGS FOR PROSTHETIC HEART VALVES

[76] Inventor: Simcha Milo, 6a Noga Street, Haifa, 34407, Israel

[21] Appl. No.: 431,767

[22] Filed: May 1, 1995

[51] Int. Cl.⁶ .................................................. A61F 2/24
[52] U.S. Cl. ........................................................ 623/2
[58] Field of Search ............................... 623/2, 900

[56] References Cited

U.S. PATENT DOCUMENTS

| | | | |
|---|---|---|---|
| 3,503,079 | 3/1970 | Smith | 623/2 |
| 3,574,865 | 4/1971 | Hamaker et al. | |
| 3,587,115 | 6/1971 | Shiley | |
| 3,763,548 | 10/1973 | Anderson | 29/445 |
| 3,839,741 | 10/1974 | Haller | |
| 4,366,581 | 1/1983 | Shah | |
| 4,535,483 | 8/1985 | Klawitter et al. | 623/2 |
| 4,790,843 | 12/1988 | Carpentier et al. | 623/2 |
| 5,035,709 | 7/1991 | Wieting et al. | 623/2 |
| 5,071,431 | 12/1991 | Sauter et al. | 623/2 |
| 5,104,406 | 4/1992 | Curcio et al. | 623/2 |
| 5,192,309 | 3/1993 | Stupka et al. | 623/2 |
| 5,397,346 | 3/1995 | Walker et al. | 623/2 |

Primary Examiner—Mary Beth Jones
Attorney, Agent, or Firm—Fitch, Even, Tabin & Flannery

[57] ABSTRACT

A suture ring assembly for a prosthetic heart valve is provided which includes a suture ring body, suture ring flange, and an interior engagement surface that are formed as a unitary structure composed of pyrocarbon material or the like. The suture ring flange extends radially outward from said suture ring body and may be of an arcuate or straight design. Moreover, the suture ring flange has a plurality of pre-fabricated holes extending axially therethrough and is particularly designed for securing the assembly to the residual heart tissue. The suture ring interior engagement surface is proportioned to surround the exterior surface of the valve body such that it can rotate relative to the heart valve body. The suture ring assembly and the valve body are specifically designed to axially engage each other so as to prevent disengagement in either axial direction. Any axial displacements that may occur during the opening and closing of the prosthetic heart valve are absorbed or dampened with spring-like, shock-absorbing mechanisms formed as part of a retaining ring which is part of the suture ring assembly.

20 Claims, 5 Drawing Sheets

SUTURE RINGS FOR PROSTHETIC HEART VALVES

FIELD OF THE INVENTION

The present invention relates to suture rings for implanting heart valve prostheses and more particularly to improved suture rings configured to facilitate insertion of a heart valve in a patient, which are adapted to inhibit excessive tissue growth proximate the heart valve.

BACKGROUND OF THE INVENTION

A wide variety of heart valve prostheses have been developed to operate in conjunction with the pumping action of the heart to take the place of defective natural valves. These valves variously have valve bodies which are designed to function with one or more occluders or leaflets to open and close a central blood flow passageway through the valve body.

As a means for inserting heart valves into the heart, the valves commonly have attached fabric members suturable to the tissues of the heart. Frequently the fabric member is attached to a separate suture ring which is applied to the periphery of the heart valve body or orifice ring, for example, as described in U. S. Pat. Nos. 3,763,548 and 4,535,483. Conventional sewing rings or suture rings are made of Dacron (™) fabric which enables a surgeon to suture the prosthetic valve to the residual valve ring after the defective valve has been removed. However, there is some incidence of failure of mechanical heart valves that is attributed to tissue overgrowth from the fabric members into an interference location with the moving mechanical parts of the heart valves.

Another important design consideration for heart valves and their suture rings is minimizing the radial thickness in order to maximize the size of the central blood flow passageway of the heart valve that is inserted in a patient's natural passageway. Thinner heart valve bodies formed, for example, as unitary structures of pyrolytic carbon have enabled larger valve passageways to be provided; however, thin heart valve bodies sometimes lack the rigidity that is desirable for such valves. To improve the stability and rigidity of the heart valve body, the outer surface of many heart valve bodies are often formed with a shallow groove or channel which receives a metal stiffening ring for the valve body, which is otherwise preferably made of a material having some resiliency, such as pyrocarbon or pyrocarbon-coated graphite.

Some existing heart valve and suture ring combinations must be assembled and pre-oriented prior to surgical insertion within the patient. Such pre-orientation contributes to the difficulty associated with the surgeon's task of obtaining the proper fit and proper orientation of the heart valve and suture ring during the insertion operation. A preferable design should allow for easy insertion into the patient after which it may be easily adjusted or oriented to the proper position for suturing to heart tissues.

The opening and closing of heart valves should be sufficiently soft so that the patient is not disturbed by the sounds produced and that the forces imparted on the heart walls are minimal. Nevertheless, the opening and closing of most existing heart valves does impart small axial forces on the valve body which often translate into small axial displacements or deformations of the valve body. The traditional Dacron (™) fabric rings also provide a cushion for the harsh impact on the mechanical parts as the valve closes. To that end, the heart valve body in combination with the suture ring should therefore provide sufficient dampening or resistance to these small axial displacements.

Accordingly, there is a continuing need for improved suture rings which together with the heart valve bodies occupy a narrow region along the heart passageway and can be easily inserted and adjusted within the patient. Further, the heart valve bodies and suture rings which together provide the rigidity needed to assure that the valve body will not be radially deformed during insertion and that axial displacements during valve operation are sufficiently dampened or absorbed. More importantly, the suturing member portion of the improved suture ring should be adapted to prevent or inhibit tissue growth thereon.

SUMMARY OF THE INVENTION

The present invention provides a suture ring assembly for a prosthetic heart valve. The preferred suture ring assembly and heart valve body includes a suture ring, a suture ring flange for securing the assembly to the residual heart tissue, an engaging means between the suture ring and the valve body, a retaining means, and a dampening means. Preferably, the suture ring and suture ring flange form a unitary structure composed of pyrocarbon material wherein the suture ring flange extends radially outward from said suture ring and includes a plurality of holes extending axially therethrough. The suture ring flange is particularly designed for securing the assembly to the residual heart tissue and may be of an arcuate configuration or of a straight configuration.

In one aspect of the invention, the suture ring has an interior surface that is dimensioned or proportioned to surround the exterior surface of the valve body such that it can freely rotate relative to the valve body. The engaging means, or more accurately, the interengaging means preferably includes a circular protrusion extending radially inward from said interior surface of said suture ring and a circular ledge protruding from said exterior surface of said valve body. These two structures are adapted to axially interengage so as to prevent disengagement of the suture ring assembly and heart valve body in one axial direction. These structures are further designed such that the suture ring rotates in bearing contact with said circular ledge of said valve body. The retaining means is preferably in the form of retaining rings that maintain axial engagement between said valve body and said suture ring so as to prevent disengagement in the other axial direction. Any axial displacements that may occur during the opening and closing of the prosthetic heart valve are optionally absorbed or dampened with spring-like shock-absorbing mechanisms.

The present suture ring assembly for use with prosthetic heart valves realizes the aforementioned objects, features and advantages in a manner that is clearly evident from a thorough consideration of the detailed description when taken in conjunction with the drawings wherein there is shown and described illustrative embodiments of the invention.

BRIEF DESCRIPTION OF THE DRAWINGS

In the following detailed description, reference will be made to the attached drawings in which.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims. In addition, the general principles of the invention are also described in Disclosure Document No. 359105 filed on Aug. 5, 1994 and incorporated by reference herein.

Figure 1:
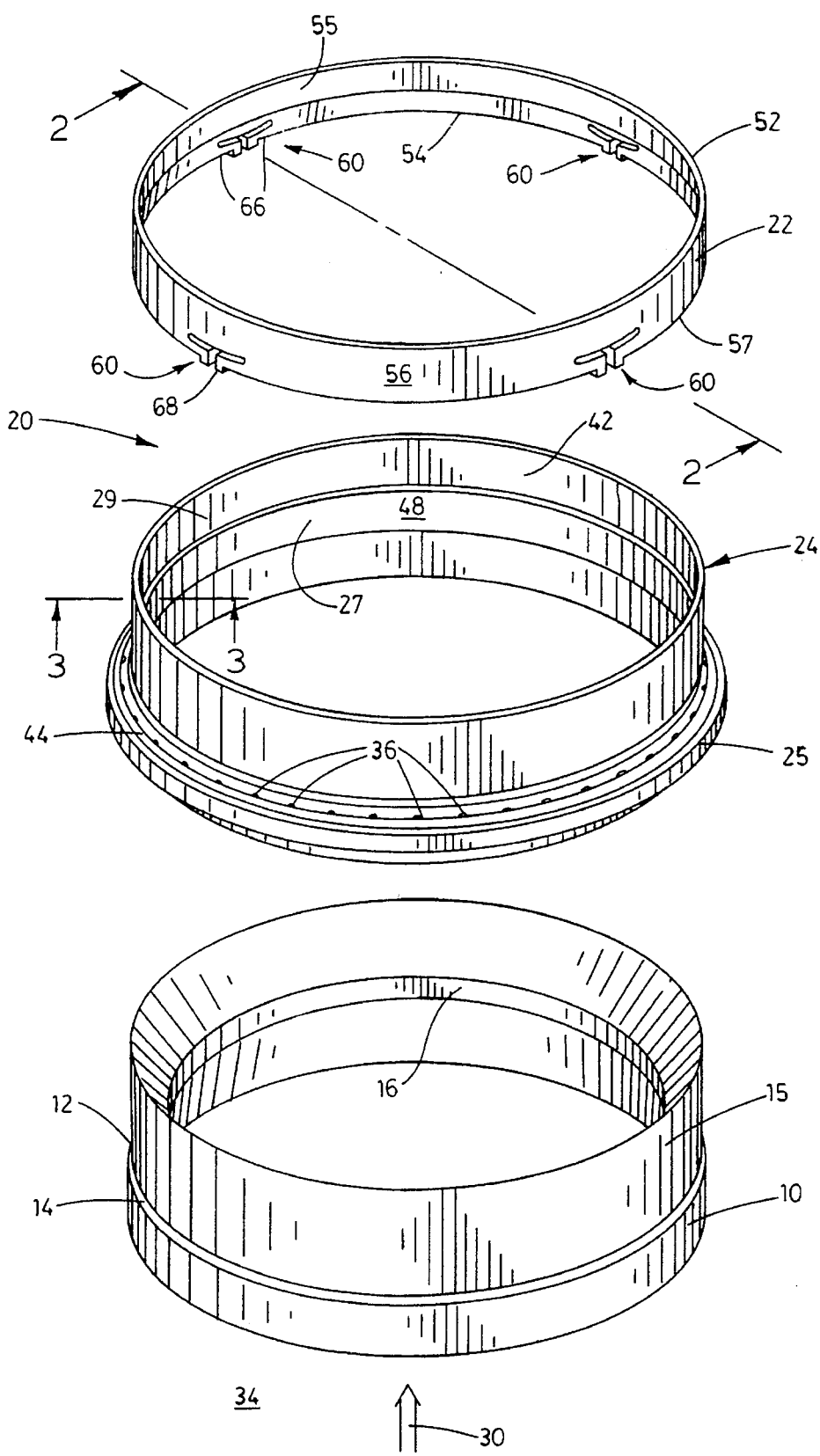
FIG. 1 is a exploded perspective view of a heart valve body and a suture ring assembly, embodying various features of the invention, for insertion in a mitral location.
Figure 2:
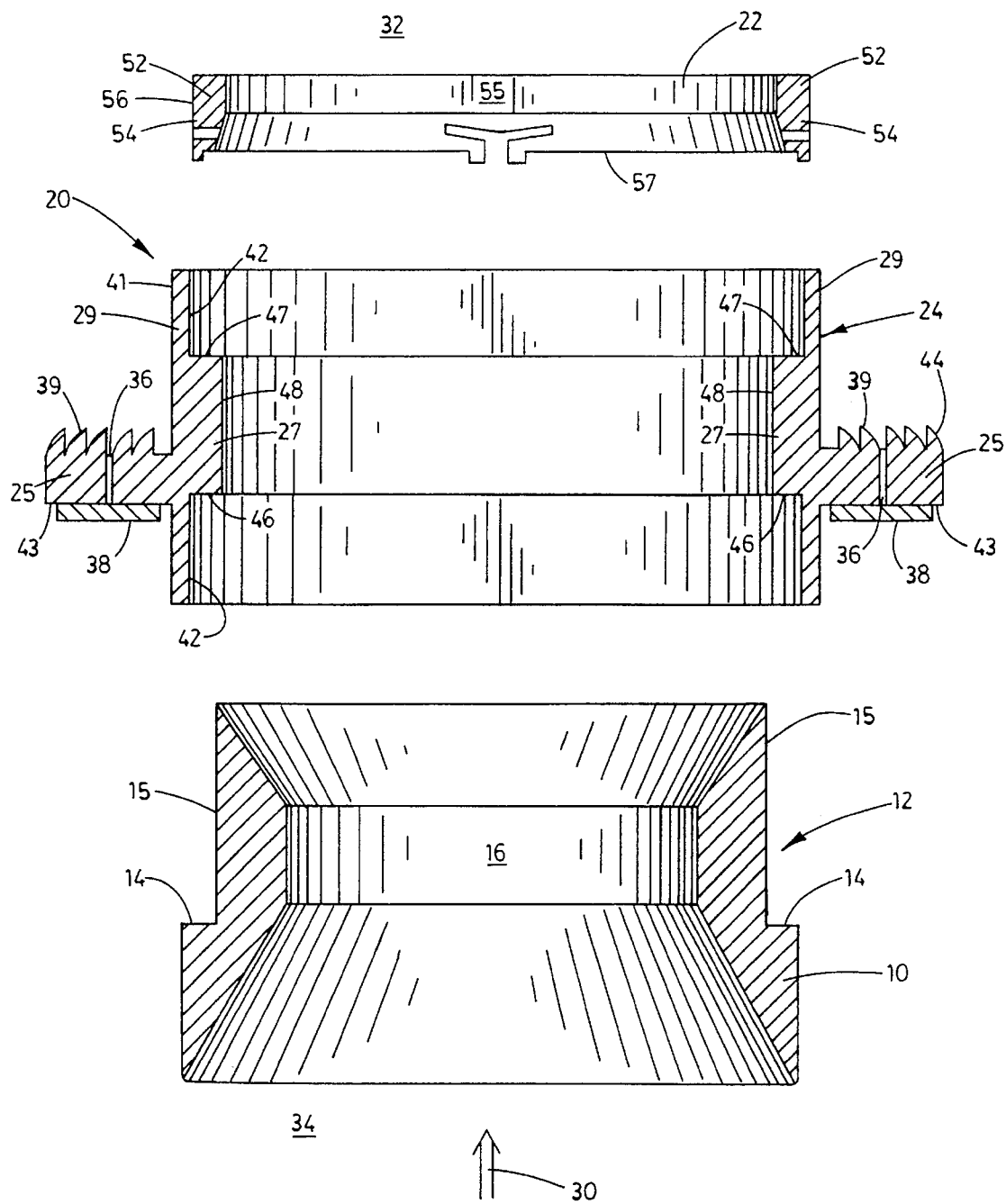
FIG. 2 an exploded cross-sectional view of the heart valve body and suture ring assembly of FIG. 1.

Referring to FIG. 1 and FIG. 2, there are illustrated perspective and cross section views of a first embodiment of the heart valve body 10 and suture ring assembly 20 particularly adapted for insertion in a mitral location. The suture ring assembly 20 includes a retaining ring 22 and a suture ring 24. The suture ring 24 further comprises three basic elements including a suture flange 25, an interior flange 27 or protrusion and a suture ring body 29. The valve body 10, retaining ring 22, and suture ring 24 are all preferably made from pyrocarbon or pyrocarbon coated substrates as is commonly used in the art. More importantly, the suture flange 25 portion of the suture ring 24, in the preferred embodiment, is not made from conventional fabric materials but rather is also made from pyrolytic carbon or other similar, non-porous, thromboresistant and bio-compatible material.

Alternative materials well known in the biomedical art can be used instead of pyrocarbon, such as titanium, zirconium and corrosion-resistant alloys such as Zircaloy. Appropriate strong, nonreactive ceramic materials, including zirconium oxide, zirconium nitride and zirconium carbide might also be used. If desired, many of these materials can be coated with strongly adherent exterior coatings of pyrocarbon.

Figure 3:
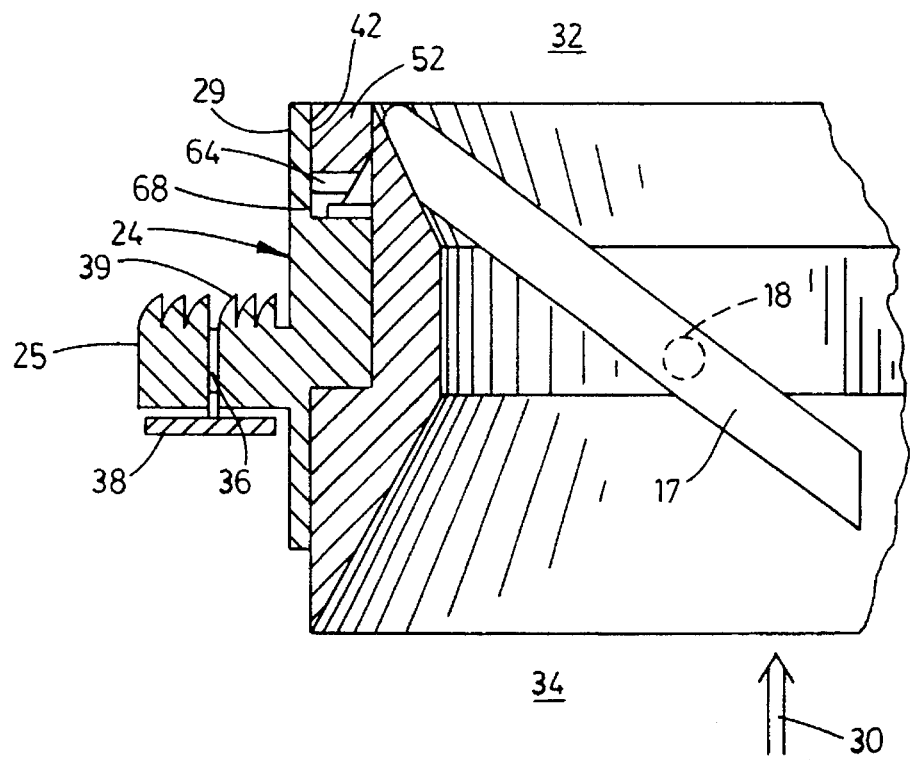
FIG. 3 is a cross-sectional view of the assembled heart valve body and suture ring assembly illustrated in FIG. 1.

Although the heart valve body 10 and suture ring assembly 20 will in use be orientated in accordance with anatomy of the heart, for ease of description, the heart valve body 10 and suture ring assembly 20 are described as having an upper or downstream end 32 and a lower or upstream end 34, as indicated by arrow 30 indicating downstream blood flow in an axial direction upward through the valve as indicated in FIGS. 1 to 3.

The heart valve body 10 generally has a shallow outwardly facing annular recess 12 forming a narrow circular ledge 14 extending outward from an exterior lateral surface 15 of the downstream portion of the valve body 10. The valve body 10 is preferably in the shape of a ring or tube having an interior surface 16, and it is often formed of materials that are somewhat resiliently radially deformable in order to facilitate the insertion of the leaflets 17 or other type of occluder means. The leaflets 17 are commonly mounted in the valve body or orifice ring 10 by suitable pivot means 18 which may include depressions and/or protuberances on the interior surface 16 of the valve body 10 and cooperating protuberances and/or depressions extending laterally from each leaflet 17. The specific pivot means form no part of the present invention.

The suture ring 24 is particularly adapted to engage and/or secure the prosthetic heart valve body 10 with the heart tissue proximate the residual valve ring after the defective valve has been removed. The preferred arrangement uses a rigid suture flange 25 extending radially outward from the exterior surface 41 of the suture ring body 29 to engage the heart tissue. Similarly, the suture ring 24 has an annular protrusion or interior flange 27 extending radially inward from an interior surface 42 of the suture ring body 29 which provides an engagement means for the prosthetic heart valve.

Preferably, the suture flange 25 has a flat annular lower surface 43, as oriented in FIG. 2, which is exposed and an annular upper surface 44 that is serrated. The upper surface 44 of the suture flange 25 faces downstream, and the lower surface 43 faces upstream with respect to the blood flow 30 through the heart valve body 10. The preferred suture flange 25 further has a plurality of prefabricated axial holes 36 equally spaced around the annular suture flange 25 which are particularly suitable for suturing the suture flange 25 to the heart tissue in the region where the defective valve was excised.

The interior flange 27 which extends radially inward from the interior surface 42 of the suture ring body 29 is preferably in the shape of an annular protrusion having an upstream surface 46, a downstream surface 47, and an interior generally cylindrical wall 48. This annular protrusion is adapted to abut the narrow circular ledge 14 formed on the exterior lateral surface 15 of the valve body 10. The upstream surface 46 of the interior flange 27 of the suture ring 24 is adapted to be seated on the narrow circular ledge 14 of the valve body 10 while maintaining sufficient clearance between the interior wall 48 and the exterior lateral surface 15 of the valve body 10 so that the valve body 10 can be rotated within the suture ring 24. The radial dimensions of the suture ring 24 and particularly the interior flange 27 as well as the radial dimensions of the valve body 10 and circular ledge 14, however, are selected so as to prevent or restrain significant lateral movements or displacements of the suture ring 24.

The rotation of the heart valve within the suture ring 24 allows the surgeon to adjust the angular orientation of the heart valve after the suture ring assembly 20 and the interconnected heart valve body 10 have been implanted within the patient during surgery. Such adjustment enables the surgeon to determine the best fit of the suture ring 24 relative to the residual heart valve tissue prior to suturing the assembly in place. After the suture ring 24 is secured in place, the valve body 10 can be forcibly rotated within the suture ring assembly 20. Such rotational adjustment enables the surgeon to properly orient the heart valve with respect to the specific chamber of the heart.

The retaining ring 22 is an annular ring dimensioned to fit in the space between the interior surface 42 of the suture ring body 29 and the exterior surface 15 of heart valve body 10 at its downstream end. As seen clearly in FIG. 3, the retaining ring 22 is situated immediately above the annular protrusion of the suture ring 24. Preferably, the retaining ring 22 is comprised of a wide first annular portion 52 and a narrower second annular portion 54. Both portions have an inwardly facing surface 55 and an outwardly facing surface 56. The wide annular portion 52 presents a tight interference fit with essentially no clearance between the inwardly facing surface 55 and the exterior surface 15 of the valve body 10. The proportions are such however that the wide annular portion 52 maintains a sliding engagement between the outwardly facing surface 56 and the interior surface 42 of the suture ring 24.

The narrow annular portion 54 of the retaining ring 22, on the other hand, includes a dampening mechanism 60 (see FIG. 1) which is seated against the downstream surface 47 of the interior flange 27. The inwardly facing surface 55 and outwardly facing surface 56 of the narrow annular portion 54 preferably maintains a small clearance with the valve body 10 as well as with the suture ring 24. The small clearance between the narrow annular portion 54 of the retaining ring 22 and exterior surface 15 of the valve body 10 assures that the dampening mechanism 60 on the retaining ring 22 operates without interference from the valve body 10. Similarly, the clearances between the narrow annular portion 54 of retaining ring 22 and suture ring 24 assure that the suture ring 24 and valve body 10 can rotate, relative to one another. In addition, such clearances allow the dampening mechanism 60 to absorb or soften impacts of heart valve openings and closures with minimal transfer of forces to the sutures.

Also seen in FIGS. 2 and 3 are several important and advantageous features of the disclosed embodiment of the suture ring assembly 20. As indicated above, the suture ring assembly 20 is preferably a solid pyrocarbon structure that is configured to enable the surgeon to suture the heart valve to the residual tissue annulus after the defective or diseased natural valve has been removed. The suture ring assembly 20 is further adapted to seal the contact areas between the patient's tissue annulus and the prosthetic valve assembly to prevent para-valvular leaks through which blood may regurgitate and possibly cause infection.

In one aspect of the present embodiment, a plurality of pre-fabricated holes 36 of an axial orientation are formed in the suture flange 25 through which the surgeon can easily insert sutures. The prefabricated holes 36 are preferably formed by laser drilling axially through the pyrocarbon suture flange 25. The laser drilling process provides smooth conduits having smooth entry and exits for the sutures, thus guarding against the sutures sustaining excessive wear over time or fraying.

Another feature is found on the upstream surface 43 of the suture flange 25, where there is optionally provided a sealing ring 38 that is adapted to prevent any leakage across the valve assembly via the prefabricated holes 36. The sealing ring 38 is preferably a thin ring made of pericard-autologous, xenopericard, Teflon, Gortex or a similar thromboresistant and bio-compatible material.

Yet another feature of the preferred embodiments is the formation of a plurality of serrations 39 on the downstream surface 44 of the suture flange 25 for the mitral valve. The downstream surface 44 represents the contact area between the patient's residual tissue annulus from which the valve was excised and the prosthetic heart valve assembly. The preferred circular serrations 39 allow the patient's residual tissue annulus to extend into the open regions between serrations upon suturing. The geometry of the circular serrations 39 wherein the radially interior surfaces are rectilinear and the exterior surfaces are curved, as best seen in FIG. 2, is such that the patient's tissue annulus resists sliding sideward after the valve assembly has been sutured in place.

Figure 4:
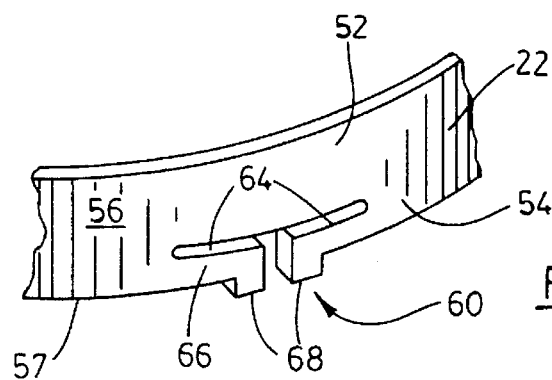
FIG. 4 is a fragmentary view of the retaining ring of FIG. 1 illustrating an enlarged view of the dampening mechanism.

Turning now to FIG. 4, there is shown an enlarged fragmentary view of the retaining ring 22 illustrating the preferred dampening mechanism 60 used with the described embodiments. The dampening mechanism 60 is formed from resilient pyrocarbon material and preferably located or formed in the lower or narrow annular portion 54 of the retaining ring 22. As seen in FIG. 4, the narrow annular portion 54 of the retaining ring 22 is located in its lower end. The preferred embodiment includes a plurality of these dampening mechanisms 60 equally spaced or located around the circumference of the lower edge 57 of the retaining ring 22. Each dampening mechanism 60 consists of a pair of oblique slits 64 formed in the lower, narrow portion 54 of the retaining ring 22. These slits 64 individually define axial displacement members 66 proximate the lower edge 57 of the narrow annular portion 54. Each axial displacement member 66 also includes a heel 68 which protrudes upstream from the remainder of the retaining ring 22. These heels 68 or extensions act to transfer the axial forces generated during the opening and closing of the heart valve to the axial displacement members 66.

The axial displacement members 66 are generally cantilevered members extending along the lower edge 57 of the retaining ring 22 and are adapted to withstand and absorb small axial displacements without transferring the axial forces or displacements to the remainder of the retaining ring 22. In the illustrated embodiment, a total of four dampening mechanisms 60 are shown with a complement of four pairs of slightly oblique slits 64 (i.e. eight slits), eight axial displacement members 66, as well as eight heels 68, although a greater or lesser number could be used. These slits 64 can be conveniently formed in a solid band using conventional laser technology.

Figure 5:
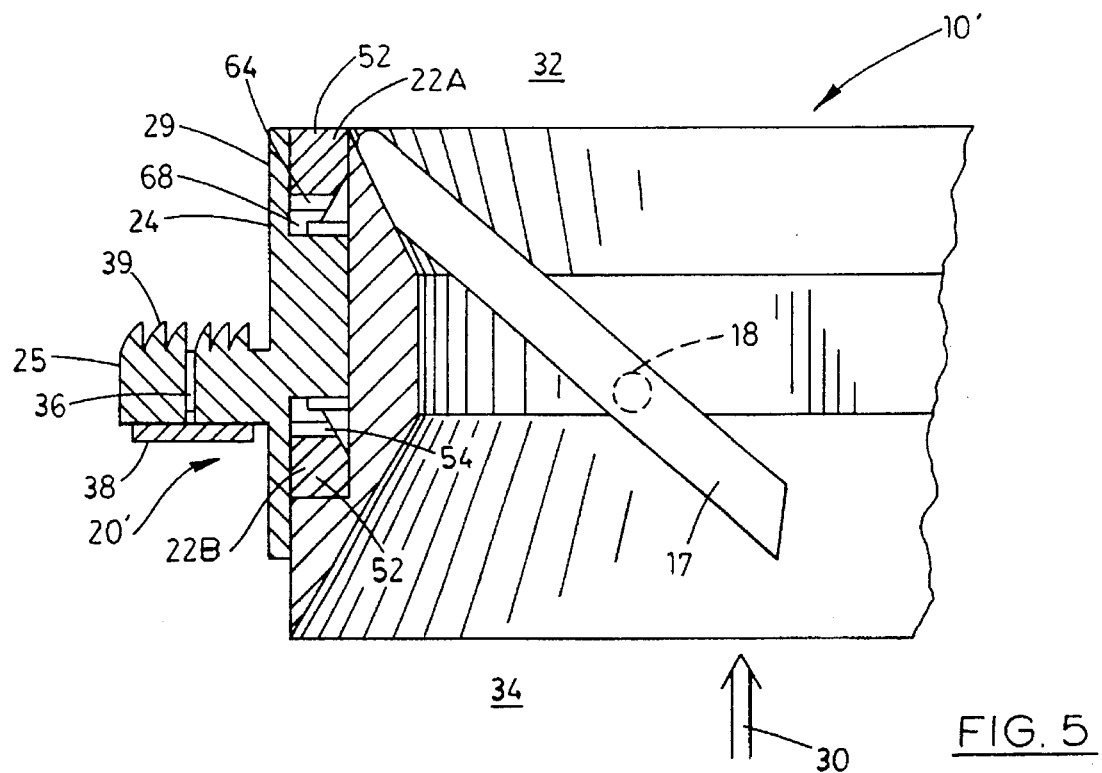
FIG. 5 is a cross-sectional view of another embodiment of the present heart valve body and suture ring assembly depicting a plurality of retaining rings.

Illustrated in FIG. 5 is another embodiment of a heart valve body 10' and suture ring assembly 20' combination having a pair of oppositely positioned retaining rings 22. Both retaining rings 22 are annular rings dimensioned to fit in the spacing between the interior surface 42 of the suture ring body 29 and the exterior surface 15 of heart valve body 10. As seen in FIG. 5, a first retaining ring 22A is situated proximate the downstream end 32 of the heart valve body 10 and suture ring assembly 20 combination. A second retaining ring 22B is situated upstream thereof adjacent the upstream annular surface 46 of the projection 27 of the suture ring body 29. Both the upper and lower annular retaining rings 22A and 22B are disposed in juxtaposition relationship with the surfaces 47 and 46, respectively, of the interior flange 27 of the suture ring 24.

As indicated above, each retaining ring 22A and 22B is comprised of an narrow annular portion 54 and a wide annular portion 52. The wide annular portion 52 has an inwardly facing surface 55 that presents a snug interference fit with no clearance against the exterior surface 15 of the valve body 10 while maintaining a sliding engagement between an outwardly facing surface 56 of the wide annular portion and the interior surface 42 of the suture ring body 29. The narrow annular portion preferably maintains a small clearance with the exterior surface 15 of the valve body 10 as well as with the interior surface 42 of the suture ring body. As before, the small clearance between the narrow annular portion 54 of the retaining rings 22A and 22B and the valve body 10 assures the spring or dampening mechanism 60 operates without interference from the valve body 10. Similarly, the clearances between the retaining rings 22 and suture ring body 29 assures that the heart valve body can be rotated within the suture ring 22 after suturing in place. In addition, such clearances allow the plurality of dampening mechanisms 60 to readily absorb or soften impacts of the heart valve opening and closing without stressing the sutures.

Figure 6:
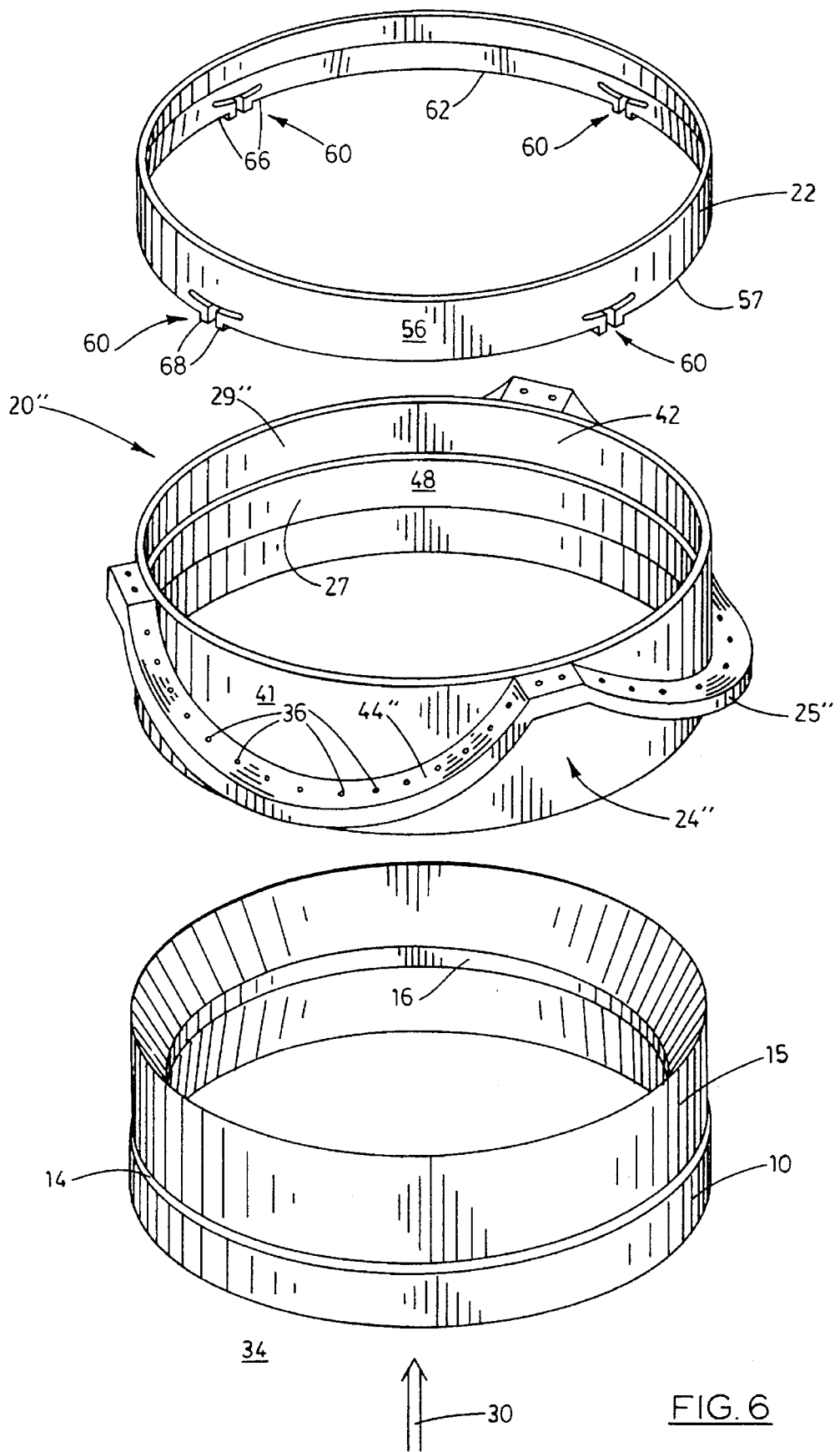
FIG. 6 is an exploded perspective view of still another embodiment of a heart valve body and a suture ring assembly for insertion in the aortic valve location.

Turning now to FIG. 6, an alternative embodiment of a heart valve body 10 and suture ring assembly 20" is illustrated. This embodiment is particularly adapted for insertion in an aortic location. This embodiment includes the same basic elements as the previous embodiments including the heart valve body 10, a suture ring 24", and a retaining ring 22 Further, as in the previous embodiments, the valve body 10, retaining ring 22, and suture ring 24" are all solid pyrocarbon structures or pyrocarbon coated substrates as is commonly used in the art. In fact, the preferred retaining ring 22 and heart valve body 10 of the aortic embodiment can be identical to the corresponding elements of the above described mitral embodiments. To that end, the descriptions thereof are omitted in the following description of the suture ring assembly 20" adapted for insertion in an aortic location.

As seen in FIG. 6, the suture ring assembly 20" includes a suture ring body 29", an undulating suture flange 25" extending radially outward from the exterior surface 41 of the suture ring body 29" and an interior flange 27 extending radially inward from the interior surface 42 of the suture ring body 29". This interior flange 27 is preferably in the shape of an annular protrusion that is adapted to be seated on the circular ledge 14 protruding from the exterior surface 15 of the heart valve body 10 with sufficient clearance so that the aortic suture ring 24" can rotate relative to the valve body 10 during the insertion procedure.

Figure 7:
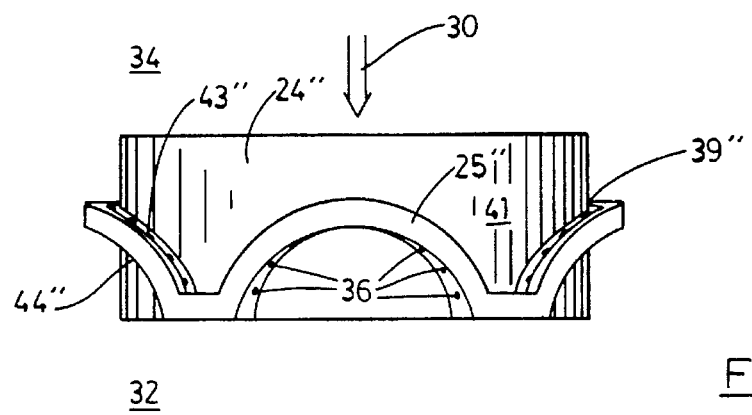
FIG. 7 is a lateral view of the suture ring assembly of the embodiment illustrated in FIG. 6 illustrating the arcuate aortic profile of the suture flange.

Referring now to FIG. 6 and FIG. 7, the suture ring 24" and suture flange 25" are constructed so that it has a undulating or tri-arcuate configuration similar to that of the residual aortic natural leaflet base. This configuration allows the suture ring 24", and more particularly the suture flange 25", to follow the anatomy of the aortic valve being replaced. Such a configuration enables a surgeon to easily suture the prosthetic heart valve assembly to the residual tissue annulus and offers a better and more durable seal in order to prevent para-valvular leaks.

The aortic suture ring 24" also preferably includes many of the advantageous features discussed with reference to the mitral suture ring. Specifically, the aortic suture flange 25" incorporates a plurality of laser drilled prefabricated axially oriented holes 36 through which the surgeon can easily insert sutures. Further, a plurality of circular serrations 39", on the upstream surface 43" of the suture flange 25" are formed to aid the patient's residual aortic valve ring tissue to become secured to the suture ring 24" because they tend to prevent the patient's tissue from escaping outward. Finally, on the downstream surface 44" of the suture flange 25", an arcuate sealing ring (not shown) may be optionally provided.

From the foregoing, it should be appreciated that the present invention thus provides an improved heart valve and suture ring assembly. Further, it will be apparent that various changes may be made in the form, construction and arrangement of the parts thereof without departing from the spirit and scope of the invention or sacrificing all of its material advantages, the forms hereinbefore described being merely exemplary embodiments thereof. Therefore, it is not intended that the scope of the invention be limited to the specific embodiments and processes described. Rather, it is intended that the scope of this invention be determined by the appending claims and their equivalents.

What is claimed is:

1. A suture ring assembly for a heart valve, said suture ring assembly comprises:

a suture ring having an interior surface proportioned to surround an exterior surface of a generally annular valve body and rotate relative to said valve body, said suture ring further adapted to axially engage with said valve body; and an annular retaining ring dimensioned to fit in a space between said interior surface of said suture ring and said exterior surface of said valve body, said annular retaining ring being adapted for maintaining engagement between said valve body and said suture ring and to prevent disengagement thereof.

2. The suture ring assembly according to claim 1 further comprising a suture ring flange extending radially outward from said suture ring and having a plurality of holes extending therethrough in a generally axial direction.

3. The suture ring assembly according to claim 2 wherein said suture ring and suture ring flange are part of a unitary structure composed of pyrocarbon material.

4. The suture ring assembly according to claim 2 wherein said suture ring flange has a plurality of serrations on a downstream surface of said suture ring flange.

5. The suture ring assembly according to claim 2 further comprising a sealing ring disposed on an upstream surface of said suture ring flange.

6. The suture ring assembly according to claim 1 wherein said suture ring further comprises a circular protrusion extending radially inward from said interior surface of said suture ring and adapted for axial engagement with a circular ledge protruding from said exterior surface or said valve body such that said suture ring rotates in bearing contact with said circular ledge of said valve body.

7. The suture ring assembly according to claim 6 wherein said retaining ring further includes a means for dampening small axial displacements of said valve body.

8. The suture ring assembly according to claim 7 wherein said dampening means further comprises:

a plurality of displacement members disposed along an edge of said retaining ring, said retaining ring having a plurality of oblique slits which define displacement cavities proximate said displacement members; and a heel axially extending from each said displacement member and engaging said circular protrusion of said suture ring;

wherein said displacement members absorb small axial displacements of said valve body by deflecting within said displacement cavities.

9. The suture ring assembly according to claim 1 wherein said retaining ring is interposed between said interior surface of said suture ring and said exterior surface of said valve body downstream with respect to said suture ring flange.

10. The suture ring assembly according to claim 1 further comprising a second annular retaining ring interposed between said interior surface of said suture ring and said exterior surface of said valve body, said annular retaining ring being disposed upstream of said suture ring flange and said second annular retaining ring being disposed downstream of said suture ring flange.

11. A suture ring and heart valve combination comprising:

a heart valve having a generally annular valve body providing a blood flow passageway and occluder means mounted within said valve body for opening and closing said passageway;

a suture ring having an interior surface constructed to surround an exterior surface of said valve body and rotate relative to said valve body, said suture ring including a circular protrusion extending radially inward from said interior surface of said suture ring, said valve body having a circular ledge protruding from said exterior surface of said valve body which axially engages said circular protrusion so as to prevent disengagement thereof in one axial direction, said suture ring being adapted to rotate in bearing contact with said circular ledge of said valve body;

an annular retaining ring located in a space between said interior surface of said suture ring and said exterior surface of said valve body for maintaining axial engagement between said valve body and said suture ring so as to prevent disengagement thereof in the other axial direction; and a suture ring flange extending radially outward from said suture ring and further having a plurality of holes extending therethrough in a generally axial direction.

12. The combination according to claim 11 wherein said suture ring and suture ring flange are a unitary structure composed of pyrocarbon material.

13. The combination according to claim 11 wherein said retaining ring further includes a means for dampening small axial displacements of said valve body.

14. The combination according to claim 13 wherein said dampening means is disposed along an edge of said retaining ring proximate said circular protrusion of said suture ring.

15. The combination according to claim 14 wherein said dampening means comprises:

a plurality of displacement members disposed along said edge of said retaining ring said retaining ring having a plurality of oblique slits which define displacement cavities proximate said displacement members; and a heel axially extending from each said displacement member and engaging said circular protrusion of suture ring;

whereby said displacement members absorb small axial displacements of said valve body by deflecting within said displacement cavities.

16. The combination according to claim 11 wherein said suture ring flange has a plurality of serrations either on an upstream surface of said suture ring flange or on a downstream surface of said suture ring flange.

17. A heart valve prosthesis comprising:

a generally annular valve body providing a blood flow passageway and occluder means mounted within said valve body for opening and closing said passageway;

a suture ring having an interior surface and being proportioned to surround an exterior surface of said valve body and rotate relative to said valve body;

said suture ring and said valve body being constructed so that disengagement thereof in one axial direction is prevented; and retaining means for preventing disengagement of said valve body and said suture ring in the other axial direction;

said suture ring having a suture ring flange extending radially outward from said suture ring which has a plurality of holes extending therethrough in a generally axial direction; and said suture ring flange having an arcuate configuration adapted to simulate a configuration of residual aortic natural leaflets.

18. A heart valve according to claim 17 wherein said retaining means comprises an annular retaining ring located in a space between said interior surface of said suture ring and said exterior surface of said valve body.

19. A heart valve according to claim 18 wherein said valve body is formed with a circular ledge, and said suture ring is formed with a radially inwardly extending circular protrusion, which together prevent disengagement in said one axial direction.

20. A heart valve according to claim 18 wherein said retaining ring is proportioned to form a tight interference fit with said exterior surface of said valve body and has dampening means formed along an edge thereof which lies proximate a downstream surface of said circular protrusion of said suture ring, said dampening means being designed to absorb small axial displacements of said valve body.

* * * * *